(12) United States Patent
Ju et al.

(10) Patent No.: US 9,347,941 B2
(45) Date of Patent: May 24, 2016

(54) DIAGNOSIS KIT FOR RHEUMATOID ARTHRITIS

(71) Applicant: CATHOLIC UNIVERSITY INDUSTRY—ACADEMIC COOPERATION FOUNDATION, Seoul (KR)

(72) Inventors: Ji-Hyeon Ju, Yongin-si (KR); Young-Kyun Kim, Seoul (KR)

(73) Assignee: CATHOLIC UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/371,792

(22) PCT Filed: Oct. 31, 2012

(86) PCT No.: PCT/KR2012/009055
§ 371 (c)(1),
(2) Date: Jul. 11, 2014

(87) PCT Pub. No.: WO2013/105721
PCT Pub. Date: Jul. 18, 2013

(65) Prior Publication Data
US 2015/0080245 A1    Mar. 19, 2015

(30) Foreign Application Priority Data

Jan. 13, 2012 (KR) .................. 10-2012-0004206
Oct. 31, 2012 (KR) .................. 10-2012-0122161

(51) Int. Cl.
*G01N 33/00* (2006.01)
*G01N 33/564* (2006.01)

(52) U.S. Cl.
CPC ........ *G01N 33/564* (2013.01); *G01N 2800/102* (2013.01)

(58) Field of Classification Search
None
See application file for complete search history.

(56) References Cited

U.S. PATENT DOCUMENTS

| | | | |
|---|---|---|---|
| 5,420,016 A * | 5/1995 | Boguslaski et al. | 435/12 |
| 8,519,096 B2 | 8/2013 | Ling et al. | |
| 2003/0157580 A1* | 8/2003 | Hochstrasser et al. | 435/7.93 |
| 2009/0117584 A1 | 5/2009 | Toes et al. | |
| 2011/0243945 A1 | 10/2011 | Raats et al. | |
| 2011/0244492 A1* | 10/2011 | Ossetrova | 435/7.92 |
| 2011/0250701 A1 | 10/2011 | Kim et al. | |
| 2014/0308676 A1* | 10/2014 | Fert-Bober et al. | 435/7.1 |

FOREIGN PATENT DOCUMENTS

| | | |
|---|---|---|
| KR | 1020020061794 | 7/2002 |
| KR | 10-1067817 | 4/2010 |
| KR | 10-2011-0015035 | 2/2011 |
| WO | 2010-117694 | 10/2010 |

OTHER PUBLICATIONS

Kuhn et al., Antibodies against citrullinated proteins enhance tissue injury in experimental autoimmune arthritis, The Journal of Clinical Investigation, vol. 116, No. 4, Apr. 2006, pp. 961-973.*
Chang et al., Citrullination of fibronectin in rheumatoid arthritis, Rheumatology 2005; 44, pp. 1374-1382.*
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992.*
R. L. Nienhuls, E. Mandema, A New Serum Factor in Patients with Rheumatoid Arthritis; the Antiperinuclear Factor. Ann Rheum Dis. 23, 302-305 (Jul. 1964).
B. J. Young, R. K. Mallya, R. D. Leslie, C. J. Clark, T. J. Hamblin, Anti-keratin antibodies in rheumatoid arthritis. Br Med J. 2. 97-99 (Jul. 14, 1979).
M. Simon, E. Girbal, M. Sebbag, V. Gomes-Daudrix, C. Vincent, G. Salama, G. Serre, The cytokeratin filament-aggregating protein filaggrin is the target of the so-called "antikeratin antibodies," autoantibodies specific for rheumatoid arthritis, J Clin Invest. 92, 1387-1393 (Sep. 1993).
M. Sebbag, M. Simon, C. Vincent, C. Masson-Bessiere, E. Girbal, J. J. Durieux, G. Serre, The antiperinuclear factor and the so-called antikeratin antibodies are the same rheumatoid arthritis-specific autoantibodies. J Clin Invest. 95, 2672-2679 (Jun. 1995).
C. Masson-Bessiere, M. Sebbag, E. Girbal-Neuhauser, L. Nogueira, C. Vincent, T. Senshu, G. Serre. The major synovial targets of the rheumatoid arthritis-specific antifilaggrin autoantibodies are deiminated forms of the alpha- and beta-chains of fibrin. J Immunol. 166. 4177-4184 (Mar. 15, 2001).
E. R. Vossenaar, N. Despres, E. Lapointe. A. van der Heijden, M. Lora, T. Senshu, W. J. van Venrooij, H. A. Menard, Rheumatoid arthritis specific anti-Sa antibodies target citrullinated vimentin. Arthritis Res Ther. 6, R142-150 (Feb. 2004).
M. Yoshida, M. Tsuji, D. Kurosaka, J. Yasuda, Y. Ito, T. Nishizawa, A. Yamada, Autoimmunity to citrullinated type II collagen in rheumatoid arthritis. Mod Rheumatol. 16, 276-281 (Oct. 2006).
A. Kinloch, V. Tatzer, R. Wait, D. Peston, K. Lundberg, P. Donatien, D. Moyes, P. C. Taylor, P. J. Venables, Identification of citrullinated alpha-enolase as a candidate autoantigen in rheumatoid arthritis. Arthritis Res Ther. 7, R1421-1429 (Oct. 19, 2005).
G. Kohler, C. Milstein, Derivation of specific antibody-producing tissue culture and tumor lines by cell fusion. Eur J Immunol. 6, 511-519 (Jul. 1976).
T. Clackson, H. R. Hoogenboom, A. D. Griffiths, G. Winter, Making antibody fragments using phage display libraries. Nature. 352, 624-628 (Aug. 15, 1991).

(Continued)

*Primary Examiner* — Gary W Counts
(74) *Attorney, Agent, or Firm* — Lex IP Meister, PLLC

(57) ABSTRACT

A method for diagnosing rheumatoid arthritis, based on the detection of citrullinated autoantigens in a test sample is disclosed. The method diagnoses rheumatoid arthritis more accurately and rapidly. Also disclosed is a kit for carrying out the method.

5 Claims, 15 Drawing Sheets
(13 of 15 Drawing Sheet(s) Filed in Color)

(56) References Cited

OTHER PUBLICATIONS

J. D. Marks, H. R. Hoogenboom, T. P. Bonnert, J. McCafferty, A. D. Griffiths, G. Winter, By-passing immunization. Human antibodies from V-gene libraries displayed on phage. J Mol Biol. 222, 581-597 (Dec. 5, 1991).

M Neidhart, S Kuchen, C Seemayer, RE Gay, BA Michel, S Gay, Expression of galectin-3 in rheumatoid arthritis synovium, 22nd European Workshop for Rheumatology Research Leiden, The Netherlands, Arthritis Res., Feb. 2002;4:A30.

E. R. Vossenaar, N. Despres, E. Lapointe. A. van der Heijden, M. Lora, T. Senshu, W. J. van Venrooij, H. A. Menard, Rheumatoid arthritis specific anti-Sa antibodies target citrullinated vimentin. Arthritis Res Ther 6, R142-150 (Feb. 2004).

* cited by examiner

Fig. 4

- Antigen : CCP
- 4 mice / 17 week schedule

Immunize Schedule table

| Initiation | Primary Injection | 1st Boosting | 1st Bleeding ELISA test | 2nd Boosting | Fusion |
|---|---|---|---|---|---|
| 2011.06.28 | 2011.06.28 | 2011.07.12 | 2011.07.13 | — | 2011.07.15 |

| | | | |
|---|---|---|---|
| 0 weeks | Injection | 12 weeks | Screening |
| 3 weeks | Fusion | 13 weeks | 3rd Cloning |
| 5 weeks | Fusion ELISA | 15 weeks | Screening |
| 6 weeks | Screening | 16 weeks | Freezing |
| 7 weeks | 1st Cloning | 17 weeks | Final Screening |
| 9 weeks | Screening | 21 weeks | Ascites (additional order) |
| 10 weeks | 2nd Cloning | | |

Fig. 5
(a)
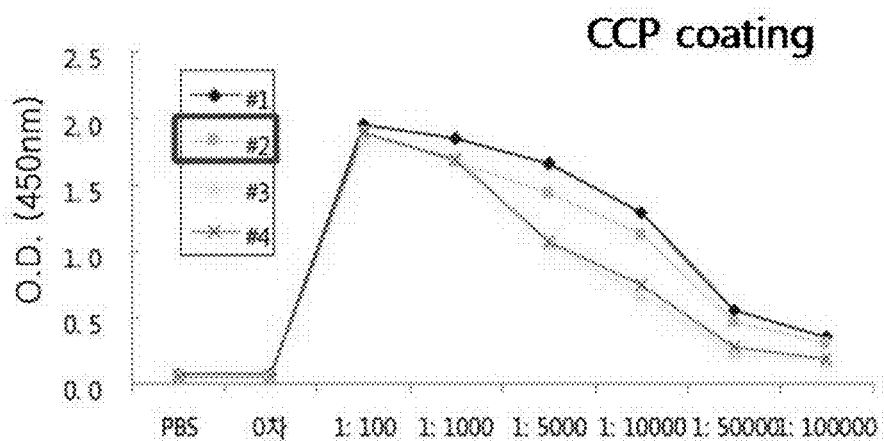
(b)
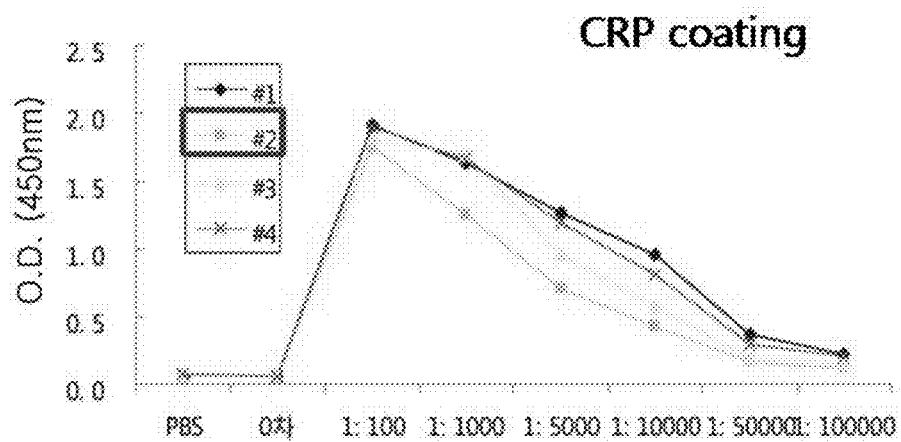

Fig. 6

Fig. 7

- CCP coating

| 1 | 1 | 2 | 3 | 4 | 5 | 6 | 7 | 8 | 9 | 10 | 11 | 12 |
|---|---|---|---|---|---|---|---|---|---|---|---|---|
| A | 0.078 | 0.079 | 0.083 | 0.086 | 0.058 | 0.085 | 0.082 | 0.086 | 0.071 | 0.073 | 0.062 | 0.101 |
| B | 0.082 | 0.071 | 0.083 | 0.083 | 0.084 | 0.117 | 0.085 | 0.071 | 0.100 | 0.078 | 0.119 | 0.091 |
| C | 0.076 | 0.094 | 0.096 | 0.079 | 0.109 | 0.075 | 0.081 | 0.082 | 0.085 | 0.087 | 0.069 | 0.073 |
| D | 0.090 | 0.104 | 0.107 | 0.076 | 0.113 | 0.064 | 0.110 | 0.076 | 0.079 | 0.259 | 0.082 | 0.090 |
| E | 0.079 | 0.071 | 0.074 | 0.104 | 0.103 | 0.103 | 0.081 | 0.088 | 0.061 | 0.091 | 0.079 | 0.091 |
| F | 0.067 | 0.090 | 0.072 | 0.074 | 0.100 | 0.074 | 0.089 | 0.083 | 0.100 | 0.077 | 0.087 | 0.076 |
| G | | 0.090 | 0.094 | 0.086 | 0.076 | 0.068 | 0.068 | 0.112 | 0.086 | 0.058 | 0.085 | 0.085 (−) |
| H | | 0.056 | 0.084 | 0.074 | 0.068 | 0.076 | 0.076 | 0.085 | 0.082 | 0.091 | 0.079 | 2.035 (+) |

- CRP coating

| 1 | 1 | 2 | 3 | 4 | 5 | 6 | 7 | 8 | 9 | 10 | 11 | 12 |
|---|---|---|---|---|---|---|---|---|---|---|---|---|
| A | 0.071 | 0.068 | 0.065 | 0.067 | 0.063 | 0.063 | 0.056 | 0.066 | 0.059 | 0.110 | 0.108 | 0.124 |
| B | 0.079 | 0.058 | 0.064 | 0.131 | 0.062 | 0.094 | 0.066 | 0.071 | 0.121 | 0.074 | 0.119 | 0.123 |
| C | 0.078 | 0.096 | 0.093 | 0.066 | 0.092 | 0.062 | 0.077 | 0.071 | 0.074 | 0.086 | 0.069 | 0.083 |
| D | 0.079 | 0.088 | 0.104 | 0.061 | 0.091 | 0.050 | 0.072 | 0.052 | 0.060 | 0.086 | 0.115 | 0.081 |
| E | 0.084 | 0.075 | 0.119 | 0.085 | 0.092 | 0.078 | 0.086 | 0.090 | 0.056 | 0.066 | 0.088 | 0.117 |
| F | 0.077 | 0.112 | 0.073 | 0.081 | 0.100 | 0.085 | 0.084 | 0.091 | 0.100 | 0.089 | 0.080 | 0.122 |
| G | 0.086 | 0.109 | 0.082 | 0.074 | 0.079 | 0.056 | 0.084 | 0.082 | 0.094 | 0.058 | 0.081 | 0.136 (−) |
| H | 0.072 | 0.067 | 0.084 | 0.103 | 0.101 | 0.094 | 0.075 | 0.081 | 0.072 | 0.083 | 0.093 | 1.817 (+) |

Fig. 8

SEQUENCE LISTING

<160> NUMBER OF SEQ ID NOS: 4

<210> SEQ ID NO 1
<211> LENGTH: 21
<212> TYPE: PRT

```
<213> ORGANISM: Artificial Sequence
<220> FEATURE:
<223> OTHER INFORMATION: CCP peptide
<220> FEATURE:
<221> NAME/KEY: VARIANT
<222> LOCATION: (9)
<223> OTHER INFORMATION: Xaa is citrulline

<400> SEQUENCE: 1

His Gln Cys His Gln Glu Ser Thr Xaa Gly Arg Ser Arg Gly Arg Cys
 1               5                  10                  15

Gly Arg Ser Gly Ser
            20

<210> SEQ ID NO 2
<211> LENGTH: 21
<212> TYPE: PRT
<213> ORGANISM: Artificial Sequence
<220> FEATURE:
<223> OTHER INFORMATION: CRP peptide

<400> SEQUENCE: 2

His Gln Cys His Gln Glu Ser Thr Arg Gly Arg Ser Arg Gly Arg Cys
 1               5                  10                  15

Gly Arg Ser Gly Ser
            20

<210> SEQ ID NO 3
<211> LENGTH: 122
<212> TYPE: PRT
<213> ORGANISM: Artificial Sequence
<220> FEATURE:
<223> OTHER INFORMATION: Heavy chain variable domain of 12G1

<400> SEQUENCE: 3

Glu Val Lys Leu Glu Glu Ser Gly Ala Glu Leu Val Arg Pro Gly Thr
 1               5                  10                  15

Ser Val Lys Ile Ser Cys Lys Ala Ser Gly Tyr Gly Phe Thr Asn Tyr
                20                  25                  30

Trp Leu Gly Trp Ile Lys Gln Arg Pro Gly His Gly Leu Glu Trp Ile
            35                  40                  45

Gly Asp Val Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Val Tyr
65                  70                  75                  80

Met Gln Leu Ser Ser Leu Thr Ser Glu Asp Ser Thr Val Tyr Phe Cys
                85                  90                  95

Ala Arg Glu Gly Gly Ile Thr Thr Ala Pro Tyr Pro Phe Gly Tyr Trp
            100                 105                 110

Gly Gln Gly Thr Leu Val Thr Val Ser Ala
            115                 120

<210> SEQ ID NO 4
<211> LENGTH: 107
<212> TYPE: PRT
<213> ORGANISM: Artificial Sequence
<220> FEATURE:
<223> OTHER INFORMATION: Light chain variable domain of 12G1

<400> SEQUENCE: 4

Asp Ile Val Met Thr Gln Thr Pro Ser Ser Met Tyr Ala Ser Leu Gly
 1               5                  10                  15
```

-continued

```
Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Trp
                85                  90                  95

Thr Phe Gly Gly Gly Thr Lys Leu Glu Ile Lys
            100                 105
```

DIAGNOSIS KIT FOR RHEUMATOID ARTHRITIS

TECHNICAL FIELD

The present invention aims to diagnose rheumatoid arthritis more accurately and rapidly, and relates to a method and a kit for diagnosing rheumatoid arthritis, based on the detection of citrullinated autoantigens in a test sample.

BACKGROUND ART

Rheumatoid arthritis (RA) is a chronic inflammation of the synovium that causes bone deformity via the progressive destruction of articular cartilage resulting in bone erosion, thus leading to a great decrease in the quality of life of persons suffering from the disease. In spite of extensive studies, the cause of RA remains unclear. Hence, it is important to provide an opportunity for early treatment of RA by rapid and accurate diagnosis before irreversible destruction of joints occurs in order to prevent bone deformity and destruction, thereby improving the prognosis and the quality of life of the patient.

Currently, the diagnosis of RA primarily depends on clinical symptoms, but is, for the most cases, carried out only after the significant progression of joint destruction. Although rheumatoid factor (RF) is adapted as a serological parameter for RA diagnosis in the international classification criteria established by the American College of Rheumotology (ACR), RF is of poor sensitivity because as high as 20% of RA patients are found to be RF negative throughout the progression of RA. Further, RF is low in specificity and it is detected in patients suffering from other rheumatoid disorders, chronic inflammation, or malignant tumors, and is even detected in some healthy persons.

Extensive research has been directed towards the development of other diagnostic markers for RA, resulting in finding the facilitation of citrullination of proteins and the presence of anti-citrullinated protein antibody (ACPA), an autoantibody against citrullinated proteins, in rheumatoid joints. Hence, ACPA is now used as a diagnostic marker for RA.

Citrullination is the conversion of the amino acid arginine in a protein into the amino acid citrulline by deimination as a result of the activity of pepdidylarginine deiminase (PAD) during post-translational modification. At a neutral pH, arginine is positively charged whereas citrulline is uncharged, so that conversion from arginine to citrulline may have crucial influence on the structure and function of the protein. For example, citrullination increases the hydrophobicity of the protein, leading to changes in protein folding, and even in pathological conditions.

The diagnosis of RA utilizing ACPA as a diagnostic marker is implemented by detecting ACPA in a specimen of interest. In detail, a citrullinated protein, for example, natural or recombinant filaggrin is attached onto micro-well plates to which specimen samples are then allocated to induce an antigen-antibody reaction which may lead to the detection of the autoantibodies in the specimens, as analyzed by ELISA.

Based on the finding of a study that highly valuates the advantage of a beta-sheet protein for antigen-antibody reactions over a linear protein structure, a cyclic citrullinated peptide derived from the filaggrin peptide rather than filaggrin itself has recently been used to detect these autoantibodies by ELISA (anti-CCP assay). Found to be superior in diagnostic performance to the conventional anti-citrullinated protein antibody assay using linear peptides, the anti-CCP assay is now predominantly employed for clinical diagnosis of RA. In practice, anti-CCP assay kits have been developed by many manufacturers and are now commercially available. In principle, the anti-CCP assay is based on ELISA wherein, for example, a recombinant human cyclic citrullinated filaggrin peptide, usually produced using a genetic engineering technique, is attached to micro-well plates to which a specimen sample is then allocated to each well to induce an antigen-antibody reaction, followed by color development with an enzyme-conjugated secondary antibody and then by reading absorbance at a certain wavelength (e.g., 400~600 nm) to determine the presence of the anti-CCP antibody in the specimen.

The anti-CCP assay is based on the premise that a small amount of citrullinated proteins relevant to RA might be present in a specimen from a RA patient, with a large amount of autoandibodies amplified against the citrullinated proteins therein. In practice, however, there are lots of autoantigens and autoantibodies irrelevant to RA in the blood of RA patients, and not all autoantigen candidates are citrullinated (FIG. 1). Further, the secondary antibodies used in the conventional anti-CCP assay kits are usually anti-mouse antibodies specific for mouse antigens, but can recognize non-specific antigens if any are in the specimen sample, giving rise to an increase in false positive errors (FIG. 2).

DISCLOSURE

Technical Problem

Aiming to accurately and rapidly diagnose rheumatoid arthritis, the present invention provides a method and a kit for diagnosing rheumatoid arthritis by detecting a citrullinated autoantibody in a specimen sample, as opposed to conventional diagnosis methods designed to detect anti-CCP antibodies in specimen samples.

Technical Solution

It is therefore an object of the present invention to provide an antigen-detecting method for diagnosing rheumatoid arthritis (RA), comprising detecting a citrullinated autoantigen in a biological sample.

It is another object of the present invention to provide an antigen-detecting method for diagnosing RA, comprising detecting autoantigens of rheumatoid arthritis in a biological sample; and detecting a citrullinated autoantigen among the detected autoantigens.

It is a further object of the present invention to provide a kit for diagnosing RA, comprising a monoclonal antibody binding specifically to a citrullinated protein, or an antigen-binding fragment thereof.

DESCRIPTION OF DRAWINGS

The file of this patent contains at least one drawing executed in color. Copies of this patent with color drawing(s) will be provided by the Patent and Trademark Office upon request and payment of the necessary fee.

FIG. 4 is a process time schedule for preparing a mouse monoclonal antibody specifically binding to CCP in accordance with the present invention.

FIG. 5 shows plots of absorbance (O.D.) values at 450 nm for anti-CCP and anti-CRP antibodies of sera from four mice twice immunized with the antigen CCP against dilution scale of the sera (1:100, 1:1000, 1:5000, 1:10000, 1:50000, 1:100000) after anti-CCP and anti-CRP ELISA: the mice were designated #1, #2, #3, #4; PBS stands for a negative control; the zero order stands for a serum before injection of the antigen to mice, and this serum was used as a negative control for setting a default value for the absence of anti-CCP antibodies in the serum.

FIG. 6 lists results of anti-CCP and anti-CRP ELISA after hybridoma cells are prepared by fusing splenocytes from the spleen of mouse #2 injected with the antigen CCP with myeloma cells (5 weeks, Fusion ELISA): each numeral represents absorbance (O.D.) at 450 nm, as converted from binding intensities at which anti-CCP antibodies recognized and bound to the target peptide CCP. The values marked with (+) and (-) are for positive and negative controls, respectively, in each experiment.

FIG. 7 list results of anti-CCP and anti-CRP ELISA after two rounds of screening hybridoma cells with CCP and CRP (10 weeks, $2^{nd}$ Cloning): each numeral represents absorbance (O.D.) at 450 nm, and the values marked with (+) and (-) are for positive and negative controls, respectively, in each experiment.

FIG. 8 lists results of anti-CCP and anti-CRP ELISA for two clones 11G1 and 12G1 selected after three rounds of screening hybridoma cells with CCP and CRP (13 weeks, $3^{rd}$ Cloning): each numeral represents absorbance (O.D.) at 450 nm, and the values marked with (+) and (-) are for positive and negative controls, respectively, in each experiment.

BEST MODE

Figure 1:
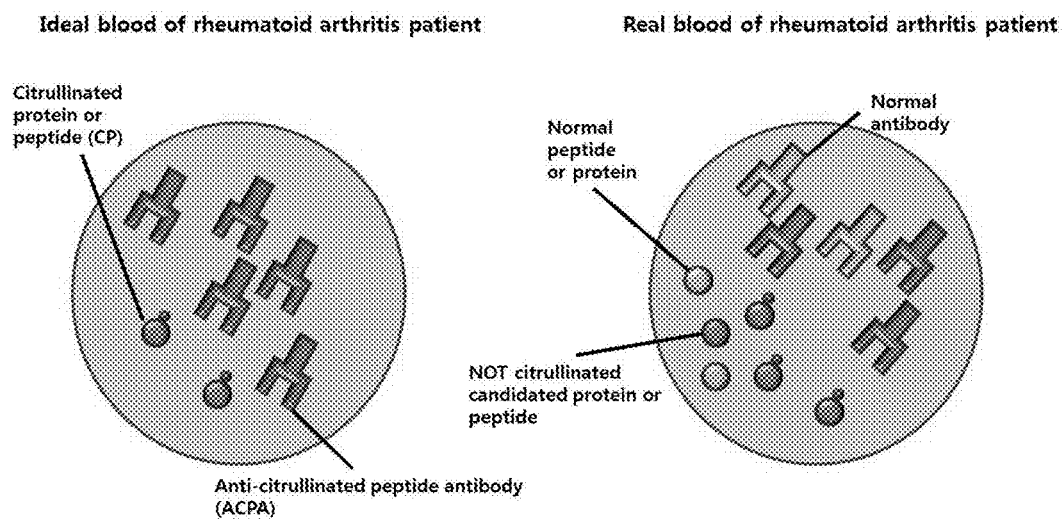
FIG. 1 is a diagram comparing the compositions between blood samples of RA patients, which is premised by a conventional anti-CCP assay and is real, respectively.
Figure 2:
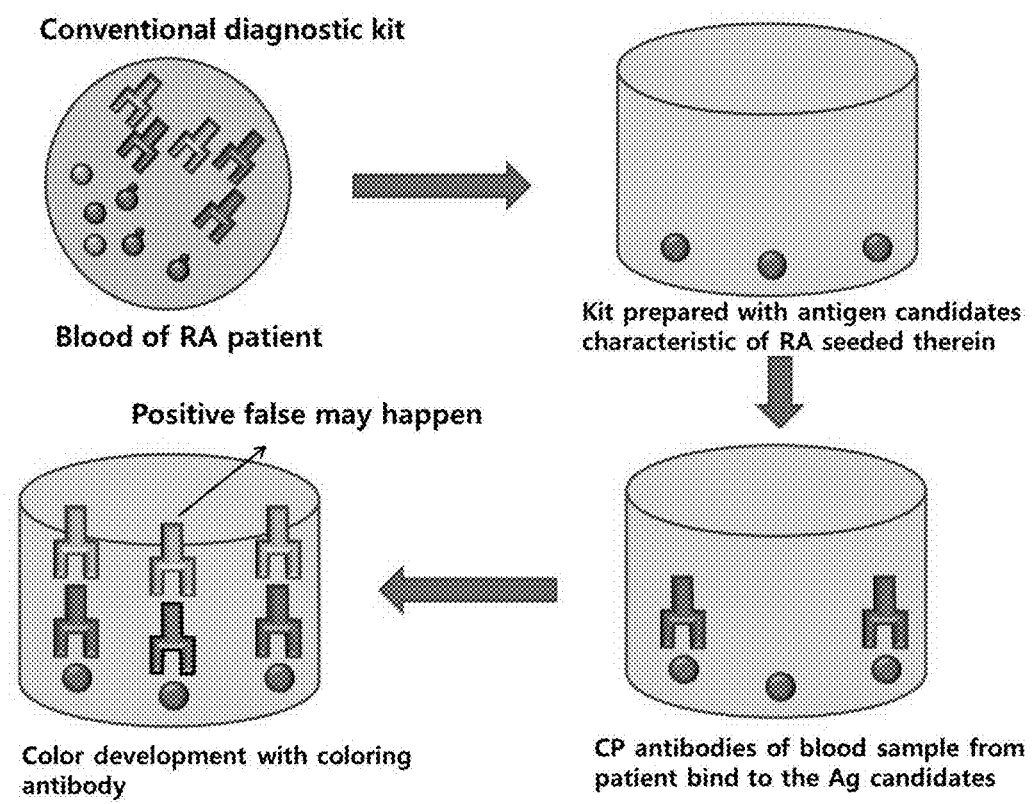
FIG. 2 is a diagram illustrating the operating mechanism and problem of the conventional diagnostic kit for RA using an anti-CCP antibody.

Commercially available anti-CCP assay kits, in current use, for diagnosis of RA are, in principle, operated in the following manner a blood sample from a patient is allowed to bind to CCP peptides coated on microtiter plates, which are provided by the manufacturers, followed by color development to qualitatively or quantitatively determine an autoantibody in the blood sample.

These anti-CCP assay kits are designed to target antibodies under the premise that the antibodies might be produced against an antigen of interest in a patient. However, direct detection of the antigen of interest could lead to more rapid diagnosis. Nonetheless, the underdevelopment of RA diagnosis techniques which are designed to directly detect an antigen of interest is because, although anti-citrullinated protein antibodies (ACPAs) are known to exist in joints of RA patients, target antigens to which the autoantibodies specifically bind still remain undefined.

For example, APF (anti-perinuclear factor; Nienhuis R L F and Mandema E A., Ann Rheum Dis 23: 302-5, 1964) and AKA (anti-keratin antibody; Young B J, et al., BMJ 2: 97-9, 1979) were reported to recognize citrullinated epitopes of filaggrin, that is, reported as ACPAs (Simon M, et al., J Clin Invest 92:1387-93, 1993; Sebbag M, et al., J Clin Invest, 95:2672-9, 1995). In practice, however, filaggrin is expressed in epithelial tissues, such as human oral mucous membrane epithelium, which are irrelevant to RA, and is thus difficult to define as a target antigen.

There have been many studies conducted to define citrullinated proteins as target antigens of ACPA. Masson-Bessiere et al. asserted that citrullinated fibrins in synovial membranes of RA patients might act as a main antigen of ACPA (J. Immunol., 2001, 166:4177-84). Nogueira et al. reported high specificity and sensitivity of citrullinated fibrinogen in detecting ACPA from serum (Arthritis Res., 2002; 4: A30). In addition, Despres et al. reported that Rheumatoid arthritis-specific anti-Sa antibodies recognize citrullinated vimentin (Arthritis Res., Ther 2004, 6:R142-50). A report of Baeten et al. has it that intracellular citrullinated proteins exist, together with ACPA, in the synovial membrane of RA patients (Arthritis Rheum., 2001, 44:2255-62). Autoimmunity to citrullinated collagen in rheumatoid arthritis was demonstrated by Mamoru Yoshida et al. (Mod Rheumatol, 16:276-281, 2006). Kinloch et al. identified citrullinated α-enolase as a candidate autoantigen in rheumatoid arthritis (Arthritis Research & Therapy, 7:R1421-29, 2005).

As such, citrullinated proteins that are found to act as autoantigens relevant to rheumatoid arthritis may be exemplified by filaggrin, fibrin, fibrinogen, vimentin, collagen, and α-enolase, and considering studies on other citrullinated proteins, it is highly expected that additional autoantigen candidates will be discovered.

However, these autoantigens are present in small quantities. Particularly, since antigens which autoantibodies found in RA patient targets are useful only under the premise that they have undergone the specific mutation citrullination, detection of uncitrullinated antigens or recognition of molecules that are, although citrullinated, unknow as autoantigens in rheumatoid arthritis may result in undesired diagnosis. In practice, therefore, there are lots of difficulties in detecting antigens indicative specifically of rheumatoid arthritis.

To overcome these practical problems, the present inventors conducted research and developed a method and kit for diagnosing RA in the new way by detecting a citrullinated autoantigen characteristic of RA, the approach being different from a conventional way of detecting an autoantibody.

In accordance with an aspect thereof, the present invention pertains to an antigen-detecting method for diagnosing RA, comprising detecting a citrullinated autoantigen in a biological sample.

Applicable to the detection of citrullinated autoantigens are various immunological analysis techniques adapted for measuring antigen-antibody reactions examples of which include ELISA (enzyme linked immunosorbent assay), Western blotting, immunoprecipitation assay, radioimmunoassay (RIA), radioimmunodiffusion, immunofluorescence assay (IFA), immunoblotting, Ouchterlony immunodiffusion, rocket immunoelectrophoresis, immunohistostaining, complement fixation assay, FACS (fluorescence Activated Cell Sorting) and protein chip assay, but are not limited thereto.

In one embodiment, the detection of a citrullinated autoantigen in a biological sample may be achieved by treating the biological sample with a monoclonal antibody comprising a heavy chain variable region having the amino acid sequence set forth in SEQ ID NO: 3 and a light chain variable region having the amino acid sequence set forth in SEQ ID NO: 4, or an antigen binding fragment thereof, but the present invention is not limited thereto. In the context of the present invention, the monoclonal antibody may be produced by the hybridoma deposited with accession No. KCLRF-BP-00276.

In accordance with another aspect thereof, the present invention pertains to an antigen-detecting method for the diagnosis of RA, comprising:

detecting autoantigens of rheumatoid arthritis in a biological sample; and detecting a citrullinated autoantigen among the detected autoantigens.

In this regard, first, candidates for citrullinated antigens are enriched by extracting autoantigens relevant to RA from a biological sample, and then determination is made of whether the extracted autoantigens are citrullinated or not so as to detect only citrullinated antigens out of the candidates, thereby diagnosing RA more accurately and effectively.

Likewise, various immunological analysis techniques adapted for measuring antigen-antibody reactions may be applicable to the detection of RA antigens. Representative, but not limitative, among the techniques are ELISA, Western blotting, immunoprecipitation assay, radioimmunoassay, radioimmunodiffusion, immunofluorescence assay (IFA), immunoblotting, Ouchterlony immunodiffusion, rocket immunoelectrophoresis, immunohistostaining, complement fixation assay, FACS and protein chip assay.

In a preferable embodiment, ELISA is employed. Examples of ELISA include direct sandwich ELISA using a labeled antibody recognizing an antigen bound to an antibody immobilized on a solid support; and indirect sandwich ELISA, in which a captured antigen bound to an antibody immobilized on a solid support is detected by first adding an antigen-specific antibody, and then a secondary labeled antibody which binds the antigen-specific antibody. For example, a first antibody capable of detecting an autoantigen of RA is immobilized onto a solid support and is reacted with a sample, and then a labeled second antibody specific for citrullinated antigens is allowed to capture the citrullinated antigens of the resulting antigen-antibody complexes, followed by enzymatic color development. Alternatively, a citrullinated antigen-specific second antibody is allowed to capture the citrullinated antigen of the antigen-antibody complex and then is recognized by a labeled secondary antibody, followed by enzymatic color development. The formation of the complex of a target protein with an antibody can thus be quantitatively measured so as to diagnose RA.

In another preferred embodiment, immunochromatography may be employed. For example, a diagnosis kit may be developed based on immunochromatography, where a flow of a blood sample is contacted with a first antibody capable of detecting autoantigens of RA, and then with a second antibody capable of detecting the citrullinated autoantigens so as to detect citrullinated autoantigens. This diagnosis kit may inform of the presence of a citrullinated antigen by displaying an indicative line thereon within up to tens of minutes after testing.

In addition, a protein chip may be employed when one or more antibodies against autoantigens of RA are arranged and immobilized in a high density at predetermined positions on the substrate. A biological sample is added to the protein chip to hybridize RA-relevant autoantibodies within the biological sample with the antibodies, followed by treatment with an antibody specific for citrullinated autoantigens. The resulting antigen-antibody complexes are read to identify a citrullinated autoantigen within the sample.

When it comes to Western blotting, total proteins are extracted from a sample, separated by size by electrophoresis, and then transferred onto a nitrocellulose membrane on which an antibody indicative of citrullination binds to citrullinated antigens. The resulting antigen-antibody complexes are quantitatively analyzed with a labeled antibody to determine the level of citrullinated proteins whereby the presence of RA autoantigens in the sample can be identified.

The above-mentioned embodiments are representatively illustrative of the methods for detecting RA antigens, but are not intended to limit the scope of the present invention. So long as it detects a citrullinated antigen of RA in a biological sample, any approach falls within the scope of the present invention.

Below, a detailed description is given of representative embodiments of the antigen detecting method according to the present invention to help the understanding of the present invention.

In accordance with a preferred embodiment, the present invention provides an antigen-detecting method for the diagnosis of RA, comprising:

(1) detecting autoantigens by treating the biological sample with a first antibody binding specifically to an autoantigen of rheumatoid arthritis to form an antigen-antibody complex between the first antibody and an autoantigen of rheumatoid arthritis present in the sample; and (2) detecting a citrullinated autoantigen by treating the antigen-antibody complex with a second antibody binding specifically to a citrullinated protein to detect a citrullinated antigen.

The step (1) is configured to detect autoantigens of RA present in a biological sample by forming an antigen-antibody complex between an autoantigen of RA present in the biological sample and a first antibody capable of binding to the autoantigen of RA. In this step, RA-relevant autoantigens present within a sample are primarily extracted to enrich candidates for citrullinated autoantigens, the final targets.

As mentioned above, some molecules that are relevant to RA and act as citrullinated autoantibodies of RA are known, and research continues to be conducted to identify additional autoantigen candidates. Therefore, the autoantibodies of RA useful in the present invention include filaggrin, fibrin, fibrinogen, vimentin, collagen and alpha-enolase, which are all known, but are not limited thereto. Any autoantigen that is relevant to RA may be used as a candidate.

So long as it binds to an autoantigen of RA, any antibody, whether monoclonal or polyclonal, can be used as the first antibody. It may be derived from any species.

In addition, the first antibody may not be a single kind, but two or more kinds of antibodies that recognize an RA autoantigen, and may be used in single or multiple combinations. Given that two or more first antibodies against an RA autoantigen may be used singly or in combination according to diagnosis purposes so that the individual antibodies can be utilized to determine the degrees of citrullination of corresponding antigens, it is possible to track the nature of the disease and to determine effects according to pharmaceutical treatment in a discriminative manner.

In the case when the first antibody is polyclonal, it can be produced using a well-known method in which, for example, an autoangen is injected into an animal to induce the production of polyclonal antibodies, followed by withdrawing a blood sample from the animal to obtain sera including the antibody. This polyclonal antibody may be sourced from any animal host, such as a goat, a rabbit, sheep, a monkey, a horse, a pig, cow, and a dog.

As for the first antibody being monoclonal, it can be prepared using a well-known technique such as a hybridoma method (Kohler and Milstein (1976) European Jounral of Immunology 6:511-519), or a phage antibody library (Clackson et al, Nature, 352:624-628, 1991; Marks et al, J. Mol. Biol., 222:58, 1-597, 1991).

Examples of the biological sample that can be used to detect autoantigens characteristic of RA in the present invention include, but are not limited to, tissues, cells, whole blood, plasma, serum, blood, saliva, synovial fluid, urine, sputum, lymph fluid, and intercellular fluid, with preference for blood.

After application of the biological sample to the antibody, any matter obstructive of the analysis, for example, an unbound sample may be removed by washing. For this, a suitable wash buffer with a pH of 6-9 may be used. The washing may be conducted three or more times at 0-40° C., but a suitable condition for the washing may be selected and modified by those skilled in the art.

In step (2), the antigen-antibody complex is treated with a second antibody binding specifically to a citrullinated protein to detect a citrullinated antigen. This step is intended to detect only a citrullinated antigen by determining whether the autoantigens of RA, primarily extracted in step (1), are in practice citrullinated or not.

Preferably, the second antibody useful in the present invention is a monoclonal antibody specific for a citrullinated protein. The monoclonal antibody, even though produced from any animal, does not recognize non-specific antibodies of the animal Even when the first antibody is polyclonal, the monoclonal antibody used as the second antibody does not exhibit non-specific binding, thus allowing for the exact quantitative measurement of the citrullinated antigen.

By way of example, the second antibody may be a monoclonal antibody or an antigen-binding fragment thereof, developed by the present inventors, comprising a heavy chain variable region having the amino acid sequence of SEQ ID NO: 3, and a light chain variable region having the amino acid sequence of SEQ ID NO: 4, but is not limited thereto. In addition, the monoclonal antibody may preferably be produced by a hybridoma cell deposited with accession No. KCLRF-BP-00276.

Detection of a citrullinated antigen may be achieved by quantitatively measuring the formation of an antigen-antibody complex between the citrullinated antigen and the second antibody. The amount of formed antigen-antibody complexes may be quantitatively determined using a known measurement method without limitations, for example, by measuring the signal size of a detection label.

The detection label may be loaded onto a second antibody binding specifically to a citrullinated antigen or onto a secondary antibody recognizing the second antibody.

Such a detection label may be selected from the group consisting of enzymes, to fluorescent substances, ligands, luminescent substances, microparticles, redox molecules and radioactive isotopes, but the present invention is not limited thereto. Examples of enzymes available as detection labels include, but are not limited to, β-glucuronidase, β-D-glucosidase, β-D-galactosidase, urease, peroxidase (e.g., horseradish peroxidase), alkaline phosphatase, acetylcholinesterase, glucose oxidase, hexokinase, GDPase, RNase, maleate dehydrogenase, glucose-6-phosphate dehydrogenase, invertase, luciferase, phosphofructokinase, phosphoenolpyruvate carboxylase, aspartate aminotransferase, phosphoenolpyruvate decarboxylase, and β-lactamase. Examples of the fluorescent substances useful as detection labels include fluorescein, isothiocyanate, rhodamine, phycoerythrine, phycocyanin, alophycocyanin, O-phthalaldehyde, and fluorescamine, but are not limited thereto. Illustrative, non-limitative among the ligands useful as detection labels are biotin derivatives. Examples of the luminescent substances useful as detection labels include acridinium ester, luciferin, and luciferase, but are not limited thereto. Examples of the microparticles useful as detection labels include colloidal gold, and colored latex, but are not limited thereto. Examples of the redox molecules useful as detection labels include ferrocene, ruthenium complex, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, and $[MO(CN)_8]^{4-}$, but are not limited thereto. Examples of the radioactive isotopes useful as detection labels include, but are not limited to, $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Figure 3:
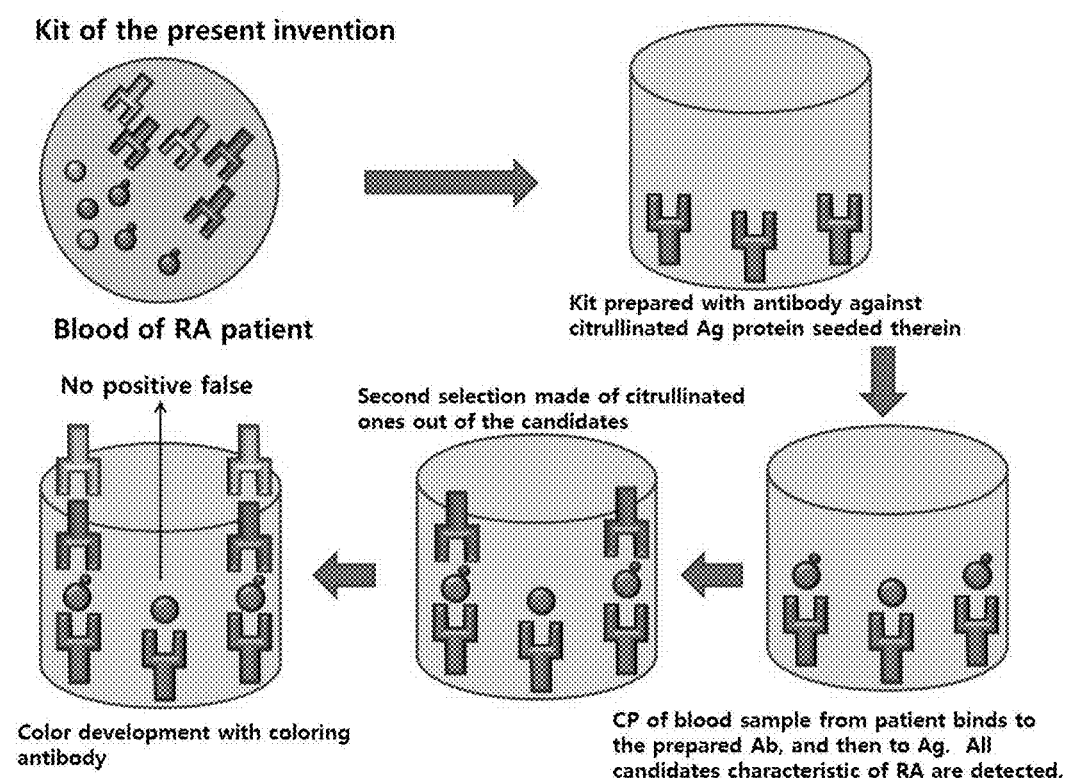
FIG. 3 is a diagram illustrating a representative operating process of a diagnostic kit for RA according to the present invention.

For a representative illustration of the method for diagnosing RA described above in accordance with the present invention, reference may be made to the schematic view of FIG. 3.

In accordance with a further aspect thereof, the present invention pertains to a composition and a kit for diagnosing RA, based on the detection of a citrullinated autoantigen characteristic of RA.

For this, the present invention provides a composition for diagnosing RA, comprising a to monoclonal antibody specifically binding to a citrullinated protein, or an antigen-binding fragment thereof in accordance with an embodiment of the present invention.

In another embodiment, the present invention provides a kit for diagnosing RA, comprising a monoclonal antibody binding specifically to a citrullinated protein, or an antigen-binding fragment thereof.

In another embodiment, the present invention provides a composition for diagnosing RA, comprising a first antibody capable of binding an autoantigen of RA, and a second antibody specifically binding to a citrullinated protein.

In another embodiment, the present invention provides a diagnostic kit for RA, comprising a first antibody capable of binding an autoantigen of RA, and a second antibody specifically binding to a citrullinated protein.

So long as it is designed to utilize an antibody specifically binding to a citrullinated protein in detecting a citrullinated autoantigen in a sample, any diagnostic kit falls within the scope of the present invention.

For example, the diagnostic kit for RA in accordance with the present invention may be based on sandwich ELISA where a first antibody and a second antibody are used in a complex, or on a strip device when a blood sample is flowed such that the antigens bind to a first antibody and a second antibody sequentially, but is not limited thereto.

In the organization of the kit according to the present invention, details of the support onto which the first antibody capable of binding to an autoantigen of RA is attached, and the second antibody specifically binding to a citrullinated protein are as described above.

Additionally, the kit of the present invention may further comprise at least one tool or reagent useful for immunological analysis selected from among a support or a suitable carrier, a marker for generating a detectable signal, a buffer, a reaction stopper, a solubilizing agent, a cleansing agent, and a stabilizing agent.

The marker for generating a detectable signal antigen-antibody complex allows for qualitative or quantitative measurement of antigen-antibody complexes, and may be exemplified by an enzyme, a fluorescent, a ligand, a luminescent, a microparticle, a redox molecule and a radioactive isotope. When the marker is an enzyme, the kit may include a substrate, a suitable buffer, a coloring enzyme or fluorescent-labeled secondary antibody, a coloring substrate, and a reaction stopper.

When horseradish peroxidase (HRP) is selected as an enzyme label, a solution of 3-amino-9-ethykarbazole, 5-aminosalicylic acid, 4-chloro-1-naphthol, o-phenylenediamine, 2,2'-azino-bis(3-ethylbenzthiazoline-6-sulfonic acid), 3,3-diaminobenzidine, 3,3',5,5'-tetramethylbenzidine, o-dianisidine, or 3,3-dimethoxybenzidine may be used as a substrate. In addition, a solution of 5-bromo-4-chloro-3-indolyl phosphate, nitroblue tetrazolium, or p-nitrophenyl phosphate may be used as a substrate, with the employment of alkaline phosphatase as an enzyme label. β-D-Galactosidae used as an enzyme label may be combined with a solution of o-nitrophenyl-β-D-galactoside or 5-bromo-4-chloro-3-indole-β-D-galactoside as a substrate. Apart from these, a variety of combinations of enzymes and enzyme coloring substrates may be employed.

In the kit of the present invention, the first antibody capable of binding to an autoantigen of RA may be provided as it is fixed onto a suitable earlier or support using various methods, as disclosed in document (*Antibodies*: A Labotory Manual, Harlow & Lane; Cold SpringHarbor, 1988). Examples of the suitable earlier include, but are not particularly limited to, PBS, polystyrene, polyethylene, polypropylene, polyester, polyacrylonitrile, fluorocarbon resin, agarose, cellulose, nitrocellulose, dextran, sephadex, sepharose, liposomes, carboxymethyl cellulose, polyacrylamide, polystyrene, gabbro, filter paper, an ion exchange resin, a plastic film, a plastic tube, a polyamine-methyl vinyl-ether-maleic acid copolymer, an amino acid copolymer, an ethylene-maleic acid copolymer, nylon, metal, glass, a glass bead, and a magnetic particle. Other solid substrates may include cell culture plates, ELISA plates, tubes and polymeric membranes. The support may have any possible form such as spherical (e.g., bead), cylindrical (e.g., inside surface of a test tube or well), or planar (e.g., sheet, test strip).

In another embodiment, the kit of the present invention may be provided in the form of an immunochomatographical strip. As a test sample (e.g. blood sample) flows throughout the strip, antigens present in the sample are sequentially bound by the first antibody and the second antibody, which may result in color development to visualize test lines, indicating the presence of a citrullinated autoantigen. For example, when a test sample is loaded to a sample receiver in the kit, autoantigens of RA within the test sample are bound by a first antibody immobilized on the sample pad and subsequently reacted with a second antibody to form a complex. Through a capillary phenomenon, the complex migrates towards the top of the membrane to which a secondary antibody is adsorbed. After association of the secondary antibody with the complex, indirect sandwich ELISA allows for the detection of citrullinated antigens. The detection may be visualized with the naked eye. In this regard, the antigen-antibody complex may be labeled with gold particles, latex particles, a fluorescent, or an enzyme. The membrane may be made of a material that is usually used for a diagnostic strep. To quote an example, a synthetic polymer, such as nitrocellulose, cellulose, polyethylene, polyethersulfone, or nylon, may be a suitable material for the membrane.

The diagnostic strip may be provided in various forms including, but not limited to, a mid-stream format where an absorption rod protruding from a plastic housing is dipped in a test sample to detect a diagnostic indicator in the body fluid; a cassette format where a small amount of a test sample is taken by a pipette and dripped to a receiver; a multi-cassette format where a plurality of cassettes are combined to simultaneously cover a plurality of test samples, and a dipstick free of a plastic housing.

In addition to being convenient because sample dilution, washing, and color development through enzyme and substrate reactions can be conducted in a single easy integrated process not requiring a special diagnostic tool. Additionally, the diagnostic method is economically beneficial due to it's rapid providing of test results.

MODE FOR INVENTION

A better understanding of the present invention may be obtained through the following examples which are set forth to illustrate, but are not to be construed as the limit of the present invention.

Example 1

Preparation of Anti-Citrullinated Antibody 1-1. Selection of Mice

After being synthesized as an antigen, the cyclic citrullinated peptide (CCP) derived from flaggrin (SEQ ID NO: 1; Arthritis Rheum 2000, 43 (1):155-163) was injected twice to each of four mice. To select mice which produce an antibody which binds to a citrullinated protein (SEQ ID NO: 1), but not to the negative control C-reactive protein (CRP; SEQ ID NO: 2), anti-CCP and anti-CRP ELISA was performed on serum from each mouse. In this regard, the CCP peptide and the CRP peptide, already prepared, were each diluted in PBS or a carbonate buffer to a final concentration of 250 ng/well. The dilution was plated in an amount of 50 μl into 96-well plates and incubated for 2 hrs at room temperature or overnight at 4° C. Each well was washed with 200 μl of PBS. To this end, the plates were overturned to decant the solution out of all the wells, and then struck down against paper towel to completely remove the remaining solution. Serum of each of the mice (#1~#4) was diluted stepwise (1:100, 1:1000, 1:5000, 1:10000, 1:50000, 1:100000), loaded in an amount of 100 μl to each well, and incubated at room temperature for 2 hrs. For negative controls, PBS and sera withdrawn before immunization were used individually. Thereafter, the washing process was repeated four times with PBS before HRP-conjugated anti-mouse IgG was added as a secondary antibody in an amount of 100 μl to each well. The antibody was diluted 1:5000 before use. The secondary antibody added to each well was incubated at room temperature for 1 hr, followed by washing four times. A residual solution, if any, was completely removed after the washing process, and an HRP substrate was added in an amount of 100 μl to each well, and incubated for 30 min under a light-tight condition to induce color development. After 30 min of the incubation, the color development was terminated with a stop solution, and color intensity was immediately measured at 450 nm in a single point photo mode. In this experiment, 3,3',5,5'-tetramethylbenzidine (TMB) was used as a substrate for generating HRP while 0.16 M sulfuric acid served as the stop solution.

Results are given in FIG. 5. In the plots of FIG. 5, steeper slopes against dilution factors correspond to poorer antigen specificity. Selection was made of mouse #2 because its specificity was high for CCP and low for CRP (FIG. 5).

TABLE 1

| Antigen | Amino Acid Sequence | SEQ ID NO: |
|---|---|---|
| Filaggrin-derived CCP | HQCHQESTXGRSRGRCGRSGS; wherein X stands for citrulline, forming a chemical bond between the two underlined "C"s. | 1 |
| CRP | HQCHQESTRGRSRGRCGRSGS | 2 |

1-2. Preparation of Hybridoma Cell

To begin with, the spleen was excised from mouse #2 producing antibodies which bound to CCP, but not to CRP, and splenocytes were isolated from the spleen, and fused with myeloma cells which were grown previously. The cell mixture was grown in a medium containing hypoxanthin, aminopterine, and thymidine (HAT medium) to selectively obtain fused cells of myeloma cells and B lymphocytes (hybridoma cells). Upon fusion, the desired hybridoma cells of myeloma cells and B lymphocytes were made while myeloma cells and B lymphocytes remained unfused or fused cells between myeloma cells themselves or between B lymphocytes themselves were obtained or both. To select the hybridoma cells only between myeloma cells and B lymphocytes from among these various cells, a mutant line of myeloma cells in which thymidine kinase (TK) and hypoxanthine guanine phosphoribosyl transferase (HGPRT) were mutated such that the mutant cells died if not fused with B lymphocytes was employed. The hybridoma cells which survived the HAT medium were grown to some degree on respective plates. Then, s hybridoma clones which were found to produce desired antibodies as observed by reaction with the antigen in media were selected using ELISA (FIG. 6).

For hybridoma selection, each of the CCP peptide and the CRP peptide, both previously prepared, was diluted to a final concentration of 250 ng/well in PBS or a carbonate buffer. The dilution was allocated in an amount of 50 μl into 96-well plates and incubated for 2 hrs at room temperature or overnight at 4° C. Each well was washed with 200 μl of PBS. To this end, the plates were overturned to decant the solution out of all the wells, and then struck down against paper towel to completely remove the remaining solution. The supernatant of the medium in which the hybridoma cells were grown was harvested, diluted 1:1000, loaded in an amount of 100 μl to each well, and incubated at room temperature for 2 hrs. Thereafter, the washing process was repeated four times with PBS before HRP-conjugated anti-mouse IgG was added as a secondary antibody in an amount of 100 μl to each well. The antibody was diluted 1:5000 before use. The secondary antibody added to each well was incubated at room temperature for 1 hr, followed by washing four times. A residual solution, if any, was completely removed after the washing process, and an HRP substrate was added in an amount of 100 μl to each well, and incubated for 30 min under a light-tight condition to induce color development. After 30 min of the incubation, the color development was terminated with a stop solution, and color intensity to was immediately measured at 450 nm in a single point photo mode. In this experiment, 3,3',5,5'-tetramethylbenzidine (TMB) was used as a substrate for generating HRP while 0.16 M sulfuric acid served as the stop solution.

Figure 8:
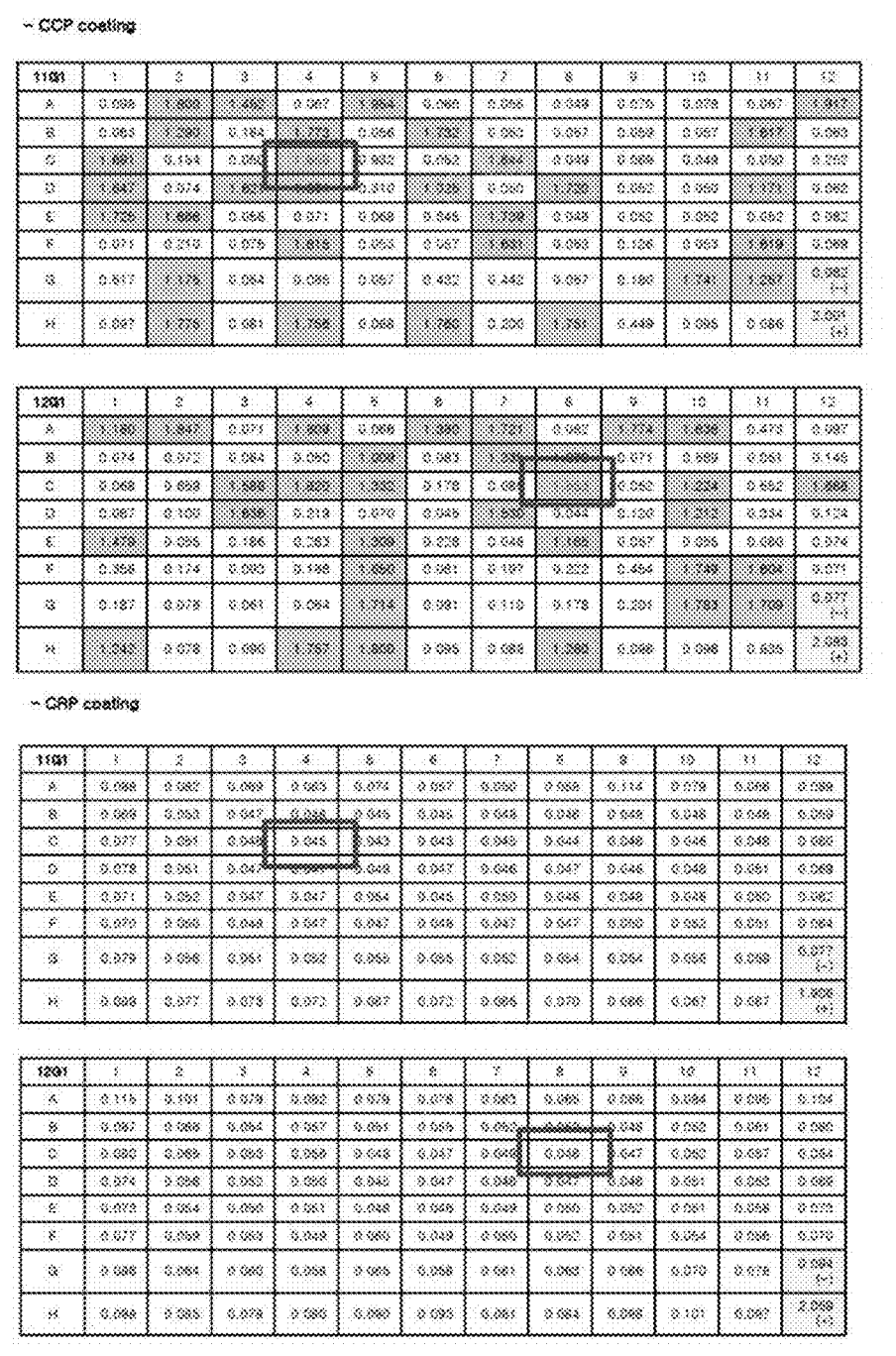

Repeated screening of the hybridoma cells against CCP and CRP left two clones 11G1 and 12G1 in the final stage (FIGS. 7 and 8). FIGS. 6 to 8 list binding intensities of anti-CCP antibodies when they recognized and bound to the target peptide CCP in each screening stage of the hybridomas, as measured by absorbance at 450 nm. The values marked with (+) and (−) are for positive and negative controls, respectively, in each experiment. With reference made to these marked values, how effectively each hybridoma clone produced an anti-CCP antibody was analyzed, and selection was made of effective clones which were then cultured many times so that the effective clones producing anti-CCP antibodies only predominated over other clones. In this way, two clones 11G1 and 12G1 were selected. Of them, 12G1 was deposited in the Korean Cell Line Research Foundation (located in the Seoul University Medical Collage Cancer Institute, 28, Yeongun-dong Jongno-Gu, Seoul) on Nov. 15, 2011, with accession No. KCLRF-BP-00276. The monoclonal antibody produced from the 12G1 hybridoma cell line was designated 12G1, and found to have the heavy chain variable region of SEQ ID NO: 3 and the light chain variable region of SEQ ID NO: 4, as analyzed for its variable regions by an automatic sequencer.

Example 2

Detection of Citrullinated Protein in RA Tissue (Immunohistochemical Staining)

With the aim of diagnosing RA by detecting citrullinated autoantigens in a test sample, the antibody 12G1 according to the present invention was analyzed for ability to specifically bind to citrullinated peptides in tissues of RA patients by immunohistochemical staining.

Paraffin-embedded tissues were sectioned at a 4 μm thickness. After deparafinization by incubation in a 60° C. dry oven for 40 min, ethanol was dripped to the tissues, with a sequential decrease in concentration (100%~70%). The tissues were washed with tap water, incubated in 3% $H_2O_2$ for 13 min, and then washed for 15 min. Because it was derived from a mouse, the 12G1 antibody was stained using VECTASTAIN Elite ABC Kit ((Mouse IgG) Catalog# PK-6102). Briefly, normal serum was blocked for 60 min, and a primary antibody was diluted 1:100, allocated to the slides, incubated overnight at 4° C., and then washed three times for 5 min with Tris buffer. After incubation with a biotinylated secondary antibody for 40 min, color development was performed for 2 min using DAB peroxidase substrate kit (Vector Lab Catalog# SK-4100), and then terminated by dipping in tap water. For background staining, the tissues were stained for 2 min with Mayer's Hematoxylin (Wako Catalog#131-09665), and then thoroughly washed with tap water. Thereafter, the tissues were mounted onto glass slides using a xylene-based mounting medium (Vector Lab Catalog# H-5000) and then observed under a microscope.

Figure 9:
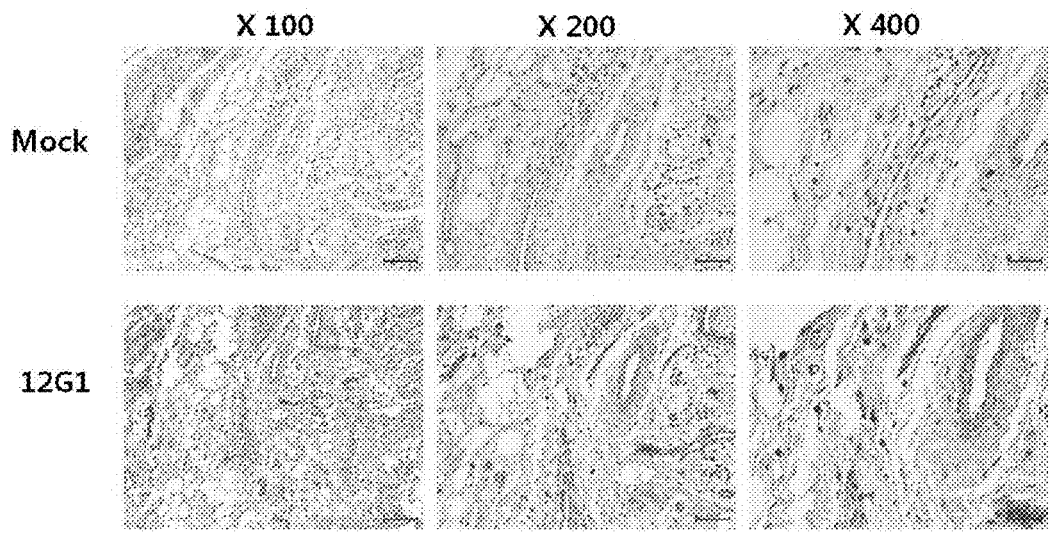
FIG. 9 shows micro-images of tissues from RA patients after immunohistochemical staining with the antibody 12G1, and a mouse IgG antibody for an isotype control (mock, structure identical, but functionless): a response to the antibody 12G1 is visualized brown, indicating the presence of citrullinated proteins.
Figure 10:
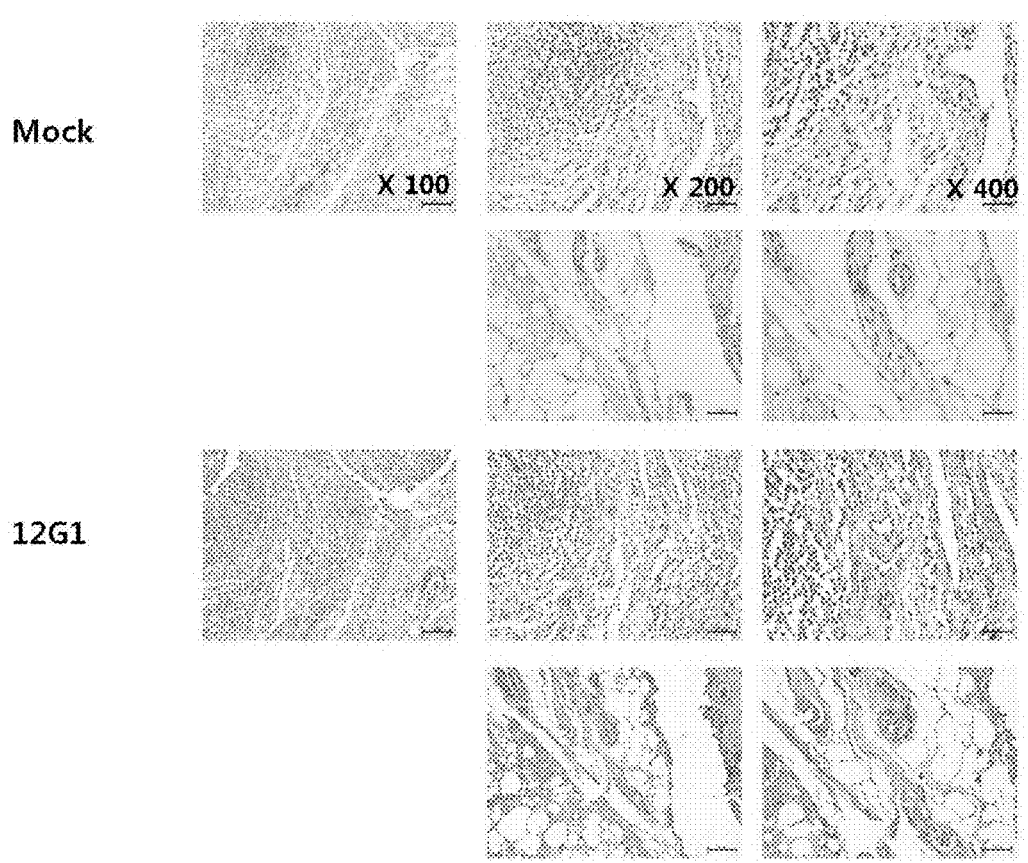
FIG. 10 shows micro-images of tissues from RA patients after immunohistochemical staining with the antibody 12G1, demonstrating the presence of citrullinated proteins.
Figure 11:
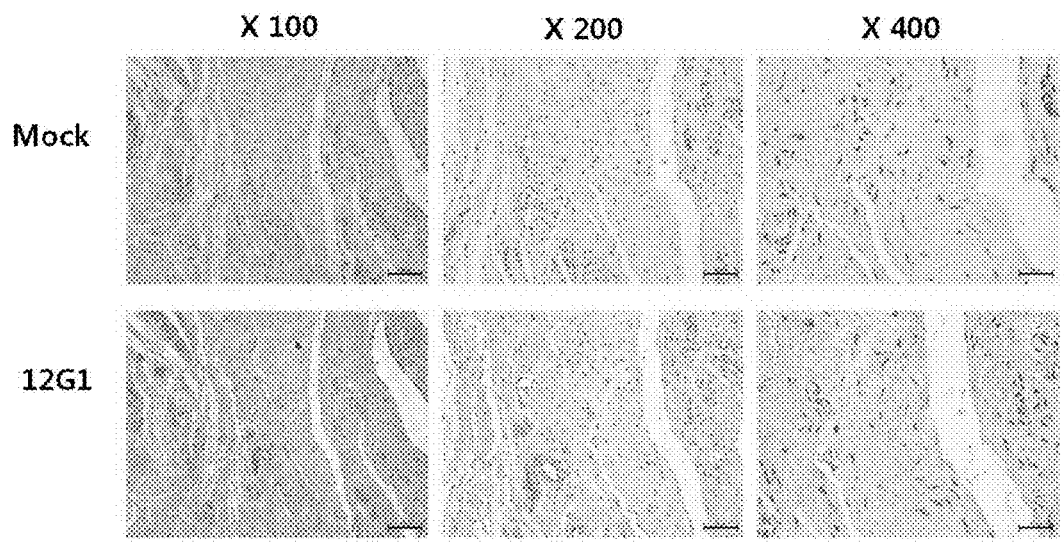
FIG. 11 shows micro-images of tissues from other RA patients after immunohistochemical staining with the antigen 12G1, demonstrating the presence of citrullinated proteins.
Figure 12:
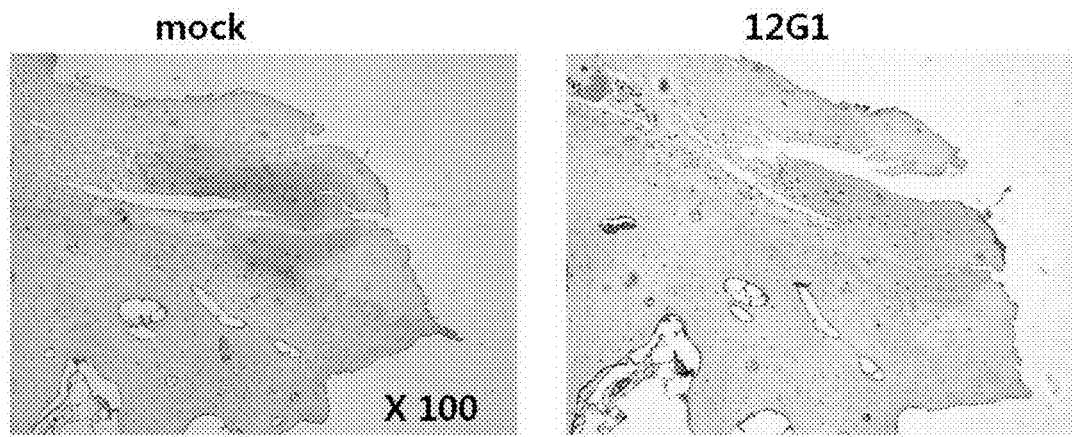
FIG. 12 shows micro-images of tissues from patients with degenerative arthritis, free of inflammation as opposed to RA, demonstrating the absence of citrullinated proteins.

As a result of a response to the antibody 12G1, brown stains were observed in all of three RA patients, demonstrating the presence of citrullinated proteins therein (FIGS. 9 to 11). On the other hand, no citrullinated proteins were detected in tissues of patients suffering from degenerative arthritis free of inflammatory responses (FIG. 12).

Example 4

Detection of Citrullinated Protein in Blood of RA Patient (Western Blotting)

With the aim of diagnosing RA by detecting citrullinated autoantigens in a test sample, the antibody 12G1 according to the present invention was analyzed for ability to specifically bind to citrullinated peptides in blood of RA patients by Western blotting.

Figure 13:
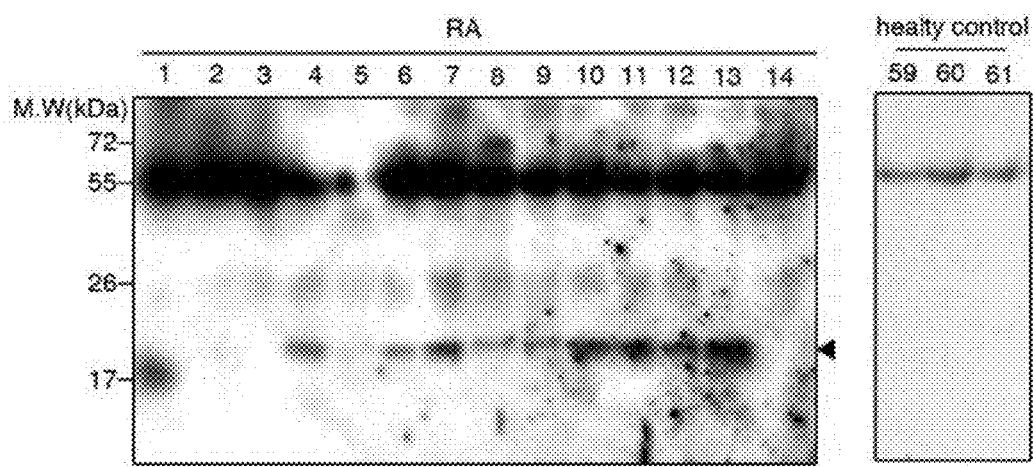
FIG. 13 shows Western blots against citrullinated antigens in blood samples from rheumatoid arthritis patients (RA) and healthy persons (HC), as detected with the pure antibody 12G1.

First, blood samples were prepared from 14 rheumatoid arthritis patients (RA) and 3 healthy controls (HC). Total proteins were extracted from each sample, and separated by size by electrophoresis. Then, they were transferred onto a nitrocellulose membrane and reacted with a citrullination-detecting antibody. In this regard, the antibody 12G1, produced from the hybridoma cell with accession No. KCLRF-BP-00276, served as the detection antibody. Conditions for the Western blotting are as follows:

12% SDS-PAGE gel, 40 ug loading
Transfer 2 h
Blocking (5% skim milk) 30 min
Primary antibody: purified antibody 12G1, or supernatant from hybridoma (KCLRF-BP-00276) culture medium
Secondary antibody: anti-mouse
Develop: exposure time 20 min FIG. 13 shows detection results of citrullinated antigens in samples using the antibody 12G1, produced from the hybridoma cell KCLRF-BP-00276, in a purified form. As can be seen in the Western blots, a band was visualized at about 17 kDa for 14 RA patients, but not detected for HC at all, demonstrating that only the citrullinated antigens present in the blood of RA patients can be detected, that is, that the antibody of the present invention has specificity for citrullinated antigens characteristic of RA.

Example 5

Assay for Diagnosis Validity of RA

In order to use the antibody 12G1 according to the present invention in diagnosing RA representative of citrullination-related disorders by detecting the presence of citrullinated autoantibodies in a test sample, an examination was made of the validity of a diagnosis kit comprising the antibody 12G1.

Diagnosis kits of RA in current use are designed to detect rheumatoid factor (RF), a serological marker for RA, or include anti-CCP diagnostic kits wherein the filaggrin-derived cyclic citrullinated peptide (CCP) is used to detect an anti-citrullinated protein antibody in serum samples.

In principle, the anti-CCP assay is based on the process in which a recombinant human cyclic citrullinated filaggrin peptide, usually produced using a genetic engineering technique, is attached to micro-well plates to which a specimen sample has been placed then allocated to each well to induce an antigen-antibody reaction, followed by determining the presence of the anti-CCP antibody in the specimen. The kit according to the present invention is different from the anti-CCP diagnostic kit in that it comprises the antibody 12G1 and detects a citrullinated antigen present in a test sample.

To examine correlation between the diagnostic kit using the 12G1 antibody according to the present invention and the conventional diagnostic kits, that is, the RF diagnostic kit and the anti-CCP diagnostic kit, statistical analysis was performed on 48 RA patients, and the results are given in Table 2, below.

As a result of statistical analysis, there was a significant correlation if $P<0.05$. As is understood from the data of Table 2, the diagnostic kit using the 12G1 to detect citrullinated antigens in a sample in accordance with the present invention was poor in correlation with the conventional RF kit, but exhibited very similar correlation with the conventional anti-CCP diagnostic kit. The RF diagnostic kit is reported to be inferior to the anti-CCP diagnostic kit in diagnostic specificity, and the kit of the present invention exhibited performance as high as that of the conventional anti-CCP diagnostic kit, and thus was found to be highly valid for RA diagnosis.

In contrast to the conventional anti-CCP diagnostic kit operating to detect antibodies present in a sample, the kit of the present invention is designed to detect citrullinated antigens present in a sample by employing the 12G1 antibody, which is a new diagnosis method which has not yet been tried. The high correlation of the kit of the present invention with the anti-CCP diagnostic kit implies that the antibody of the present invention might allow for the development of diagnosis systems guaranteeing results as good as or better than those obtained by conventional diagnosis systems.

TABLE 2

| (n = 48) | Density | P value |
|---|---|---|
| RF titer | 0.108 | 0.464 |
| CCP titer | 0.334 | 0.020 |

Example 6

Detection of RA Autoantigen and Citrullination (Sandwich ELISA)

6-1. Identification of soluble vimentin in Blood Sample

Since there have been no reports on the presence of antibodies characteristic of RA in sera themselves, examination was made of the detection of vimentin in serum by sandwich ELISA using a combination of conventional antibodies. Out of serum samples from randomly selected patients, 28 were observed to have RA as analyzed by a conventional diagnosis method while 5 patients were identified to suffer from degenerative arthritis or arthralgia, and used as negative controls. Together with them, serum samples were obtained from 5 healthy persons. As analyzed for the presence of anti-CCP antibodies by a conventional diagnosis method for RA, 28 samples of the RA patients were classified as high and low groups on the basis of an anti-CCP antibody level of 100.

Briefly, an anti-vimentin polyclonal antibody (Santa Cruz, #B2312) was diluted 1:100 in a coating buffer (cat #00-0000-53, eBioscience, 10× solution diluted to 1× in DW), seeded in an amount of 100 ul to each well of 96-well plate (Nunc maxisorp) in the evening before the day of experiment, and incubated overnight at 4° C. The next morning, each well was washed 7 times with 250 ul of a washing buffer (1×PBS, 0.05% TWEEN 20 (Poly(oxyethylene)$_n$-sorbitane-monolaurate, when "n" is usually 20). An assay buffer (cat #00-4202-55, eBioscience, 5× solution diluted to 1× in DW) was added in an amount of 200 ul to each well before incubation at room temperature for 1 hr during which the serum samples were diluted 1/10 in 1×PBS. After 1 hr of the incubation, each well was washed 7 times with 250 ul of a washing buffer. Then, the serum samples were loaded in an amount of 100 ul to each well. Serum-negative PBS and all serum samples which were antibody negative were used as controls, and loaded in mixture. After incubation at room temperature for 2 hrs, each well was washed 7 times with 250 ul of a washing buffer. Again, 200 ul of an assay buffer was added to each well, followed by incubation at room temperature for 1 hr. An anti-vimentin antibody (#ab8978, abcam) was diluted 1:100 in an assay buffer, and the dilution was added in an amount of 100 ul to each well and incubated at room temperature for 2 hrs. For the antibody negative control, the assay buffer was added instead of the antibody. Then, each well was washed 7 times with 250 ul of a washing buffer. Separately, a detection antibody (Santa Cruz, #B0310) was diluted 1:2000 in an assay buffer, and 100 ul of the dilution was added to each well, followed by incubation at room temperature for 1 hr with the plate closely sealed with foil. Again, each well was washed 9 times with 250 ul of a washing buffer. A substrate solution (1× substrate solution, cat #00-4201-56, eBioscience) was added in an amount of 100 ul to each well, and incubated at room temperature for 15 min, with the plate maintained under a light-tight condition. Thereafter, the reaction was terminated with 50 ul of a stop solution (#BMS211, eBioscience), and absorbance at 450 nm was read on Versamax (BHR06620).

Figure 14:
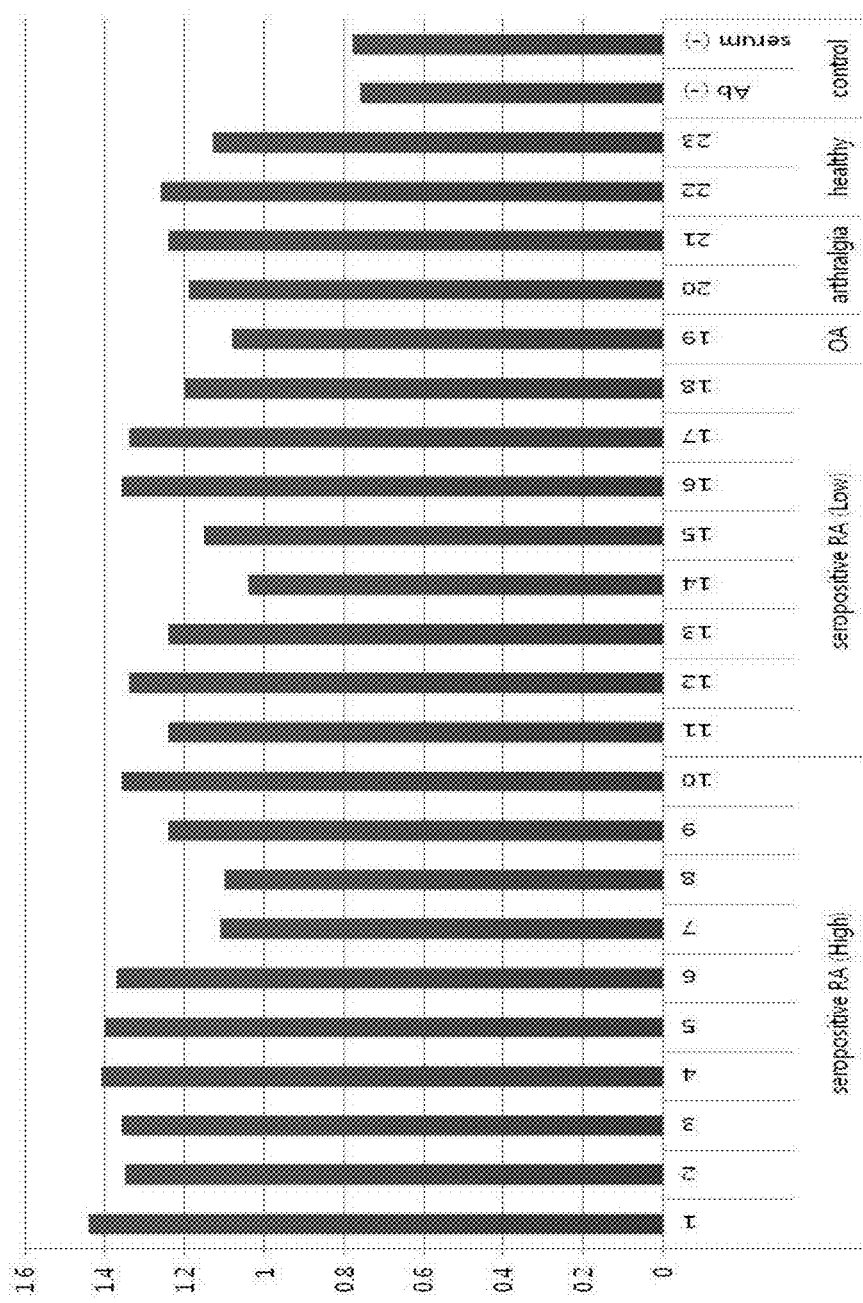
FIG. 14 is a graph showing the presence of soluble vimentin in blood samples from patients with RA, degenerative arthritis or arthralgia, and healthy persons.

PBS free of serum was used as a negative control (serum (–)) for ELISA itself while a sample made of a random mixture of the sera to be used was used as a control for detection without the secondary antibody (ab(–)). A cut-off value was set forth using these controls (red line, FIG. 14). As can be seen in FIG. 14, the analysis of the levels of vimentin in serum samples was found to allow for the detection of soluble vimentin in serum by ELISA. Based on this analysis, it was determined that there were no special differences between RA patients and healthy persons. This result has significance as basic data by which it is possible to approach a new diagnosis method for examining the citrullination of vimentin.

6-2. Identification of Citrullinated Vimentin in Blood Sample

Since it was found in the experiment of Example 6-1 that soluble vimentin could be detected in blood samples, sandwich ELISA was performed to detect citrullinated vimentin expressed in a patient-specific manner. First, antigenic substances were enriched with the primary antibody capable of capturing total vimentin as described above. Then, the antibody 12G1 developed by the present inventors was used for examining whether these substances were citrullinated. Out of serum samples from randomly selected patients, 26 were observed to have RA as analyzed by a conventional diagnosis method while 13 healthy persons were used as negative controls. As analyzed for the presence of anti-CCP antibodies by a conventional diagnosis method for RA, 26 samples of the RA patients were classified as high and low groups on the basis of an anti-CCP antibody level of 100.

Briefly, an anti-vimentin polyclonal antibody (Santa Cruz, #B2312) was diluted 1:100 in a coating buffer (cat #00-0000-53, eBioscience, 10× solution diluted to 1× in DW), seeded in an amount of 100 ul to each well of 96-well plate (Nunc maxisorp) in the evening before the day of experiment, and incubated overnight at 4° C. The next morning, each well was washed 7 times with 250 ul of a washing buffer (1×PBS, 0.05% Tween-20). An assay buffer (cat #00-4202-55, eBioscience, 5× solution diluted to 1× in DW) was added in an amount of 200 ul to each well before incubation at room temperature for 1 hr during which the serum samples were diluted 1/10 in 1×PBS. After 1 hr of the incubation, each well was washed 7 times with 250 ul of a washing buffer. Then, the serum samples were loaded in an amount of 100 ul to each well. Then, the serum samples were loaded in an amount of 100 ul to each well. Serum-negative PBS and all serum samples which were antibody negative were used as controls, and loaded in mixture. After incubation at room temperature for 2 hrs, each well was washed 7 times with 250 ul of a washing buffer. Again, 200 ul of an assay buffer was added to each well, followed by incubation at room temperature for 1 hr. The 12G1 antibody (–) for detecting citrullinated vimentin was diluted 1:100 in an assay buffer, and the dilution was added in an amount of 100 ul to each well and incubated at room temperature for 2 hrs. For the antibody negative control, the assay buffer was added instead of the antibody. Then, each well was washed 7 times with 250 ul of a washing buffer. Separately, a detection antibody (Santa Cruz, #B0310) was diluted 1:2000 in an assay buffer, and 100 ul of the dilution was added to each well, followed by incubation at room temperature for 1 hr with the plate closely sealed with foil. Again, each well was washed 9 times with 250 ul of a washing buffer. A substrate solution (1× substrate solution, cat #00-4201-56, eBioscience) was added in an amount of 100 ul to each well, and incubated at room temperature for 15 min, with the plate maintained under a light-tight condition. Thereafter, the reaction was terminated with 50 ul of a stop solution (#BMS211, eBioscience), and absorbance at 450 nm was read on Versamax (BHR06620).

Figure 15:
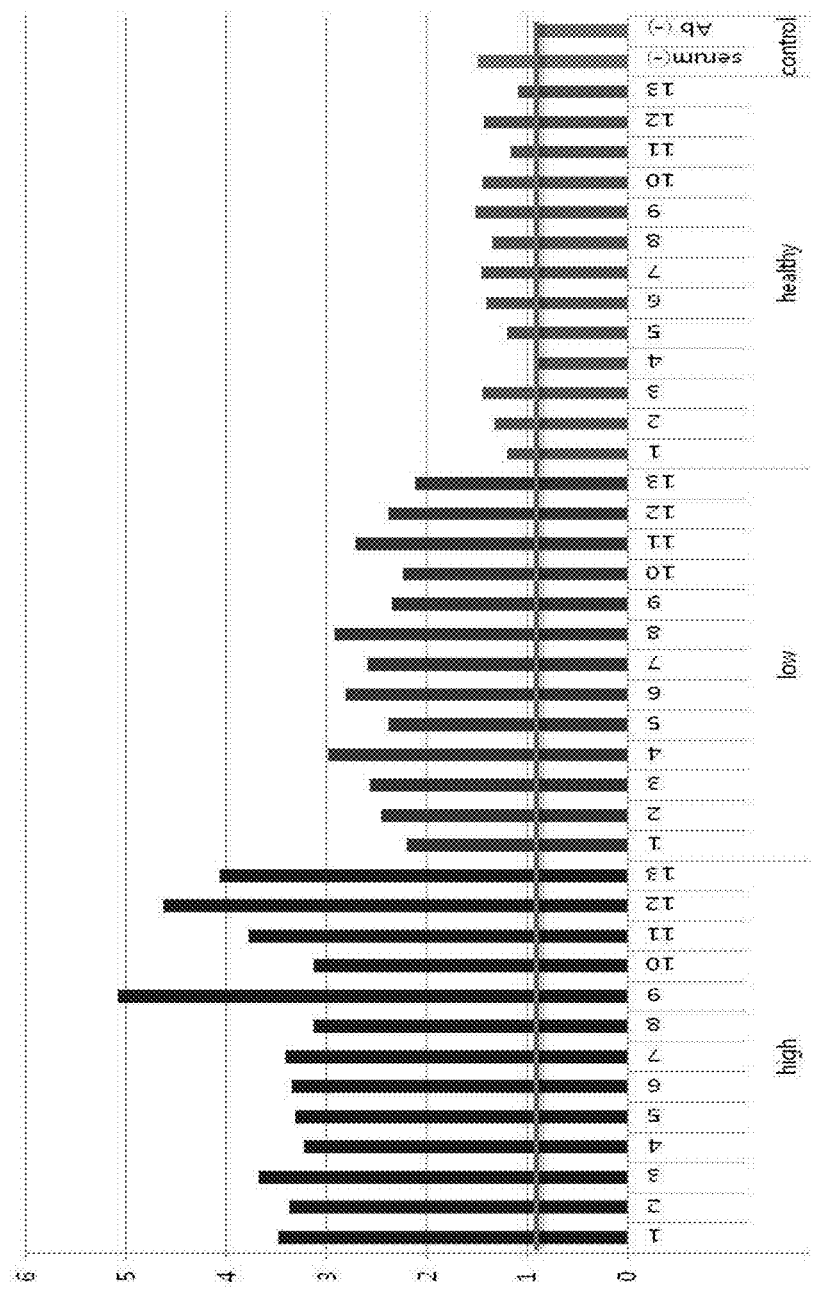
FIG. 15 is a graph showing the presence of citrullinated vimentin soluble vimentin in blood samples from patients with RA, degenerative arthritis or arthralgia, and healthy persons.

PBS free of serum was used as a negative control (serum (–)) for ELISA itself while a sample made of a random mixture of the sera to be used was used as a control for detection without the secondary antibody (ab(–)). A cut-off value was set forth using these controls (red line, FIG. 15). As can be seen in FIG. 15, the high group which was found to exhibit high levels of an anti-CCP antibody had a high level of citrullinated vimentin. Significant levels of citrullinated vimentin were also detected in the low group. Like the levels of the anti-CCP antibody, the detected levels of citrulline vimentin were different between the high group and the low group. Although the cutoff value was detected in several samples thereof, the healthy group was generally significantly different in the level of citrulline vimentin from practical patients. As is understood from the data of diagnosis, the kit according to the present invention ensured the detection of citrullinated vimentin, with results similar to those obtained by the conventional diagnostic kit using an anti-CCP antibody.

INDUSTRIAL APPLICABILITY

In contrast to conventional diagnostic methods based on the detection of anti-CCP antibodies in samples, the present invention is designed to detect citrullinated autoantigens in samples, thereby diagnosing RA more accurately and rapidly.

The invention claimed is:

1. An antigen detecting method for diagnosing rheumatoid arthritis, comprising
   (1) treating a biological sample of a human subject suspected of having rheumatoid arthritis with a first antibody binding specifically to an autoantigen of rheumatoid arthritis to form an antigen-antibody complex between the first antibody and an autoantigen of rheumatoid arthritis present in the sample; and
   (2) detecting a citrullinated autoantigen by treating the antigen-antibody complex with a second antibody comprising a heavy chain variable region having an amino acid sequence of SEQ ID NO: 3 and a light chain variable region having an amino acid sequence of SEQ ID NO: 4, or an antigen-binding fragment thereof;
   (3) measuring a level of the citrullinated antigen-antibody complex formation to diagnose rheumatoid arthritis,
   wherein the biological sample in step (1) is a tissue, a cell, whole blood, plasma, blood serum, blood, saliva, synovial fluid, urine, sputum, lymph fluid, or intercellular fluid, and
   wherein the autoantigen of rheumatoid arthritis in the step (1) is selected from the group consisting of filaggrin, fibrin, fibrinogen, vimentin, collagen and alpha-enolase.

2. The antigen detecting method of claim 1, wherein the citrullinated autoantigen is detected by an immunological assay selected from the group consisting of enzyme linked immunosorbent assay (ELISA), Western blotting, immunoprecipitation assay, immunochromatography, radioimmunoassay (RIA), Radioimmunodiffusion, immunofluorescence assay (IFA), immunoblotting, Ouchterlony immunodiffusion, rocket immunoelectrophoresis, immunohistostaining, complement fixation assay, fluorescence activated cell sorting (FACS) and protein chip assay.

3. The antigen detecting method of claim 1, wherein the second antibody is produced from a hybridoma cell deposited with accession No. KCLRF-BP-00276.

4. The antigen detecting method of claim 1, wherein the first antibody in step (1) is monoclonal antibody or polyclonal antibody.

5. The antigen detecting method of claim 1, wherein the level of the citrullinated antigen-antibody complex formation is measured by quantitatively analyzing color development with a secondary antibody conjugated with a label selected from the group consisting of an enzyme, a fluorescent, a luminescent, a microparticle, a redox molecule, and a radioisotope, said secondary antibody being able to bind to the second antibody.

* * * * *